United States Patent [19]

Moore

[11] Patent Number: Plant 6,877

[45] Date of Patent: Jun. 27, 1989

[54] *SYRINGA VULGARIS* CV MONORE

[75] Inventor: Ralph S. Moore, Visalia, Calif.

[73] Assignee: Monrovia Nursery Company, Azusa, Calif.

[21] Appl. No.: 126,111

[22] Filed: Nov. 25, 1987

[51] Int. Cl.[4] ..... A01H 5/00

[52] U.S. Cl. ..... Plt./66

[58] Field of Search ..... Plt./66

*Primary Examiner*—Robert E. Bâgwill

[57] ABSTRACT

A new and distinct selection of *Syringa vulgaris L.* (popularly known as Common Lilac) which shall be referred to hereinafter as *Syringa vulgaris* cultivar Monore. *Syringa vulgaris* cultivar Monore differs distinctively from other lilacs by a unique combination of profuse blooming at an early age, flowering well in hot areas with little winter chilling required, or flowering well in the colder typical lilac growing areas and the two toned coloring of the purple buds that open to deep purple blue flowers.

1 Drawing Sheet

DISCOVERY

This invention relates to a new and distinct selection of *Syringa vulgaris,* a member of the Oleaceae or olive family. *Syringa vulgaris* cv. Monore was selected by me from a group of seedlings at Sequoia Nursery, 2519 E. Noble Avenue, Visalia, Calif., in 1965. This plant is a seedling of *Syringa vulgaris* cv. Esther Staley which was growing in a group which included *Syringa vulgaris* cv. Mr. Lincoln and *Syringa vulgaris* cv. Ludwig Spaeth. Thus the parentage of my new plant is *Syringa vulgaris* cv. Esther Staley crossed with unknown. The plant to date is known only to exist within the boundaries of Sequoia Nursery and Monrovia Nursery Company, 18331 East Foothill Boulevard, Azusa, Calif.

REPRODUCTION

My new selection has been strictly asexually reproduced by cuttings at Monrovia Nursery Company. The distinct phenotypic characteristics of this new selection that set this plant apart from other syringa plants could be lost genetically through sexual reproduction. Therefore, sexual reproduction is prohibited and propagation is restricted to asexual reproduction by cuttings. Seed progeny from the new selection has not been observed.

BRIEF DESCRIPTION OF THE DRAWINGS

The accompanying illustration shows a typical specimen of this plant according to this invention and is depicted in color as nearly true as possible. The illustration depicts a closeup of the large 12.5 centimeter (5 inch) long by 9 centimeter (3½ inch) wide inflorescence exhibiting the purple bud color prior to the flower opening.

DESCRIPTION

Below is a detailed description of the new *Syringa vulgaris* cv. Monore, the color terminology is from The British Horticultural Colour Charts.

Overall size and habit: Deciduous shrub, dense, upright habit, After 5 to 7 years expected growth habit is 6 to 8 feet tall with a spread of 5 to 6 feet.

Flower: Profuse, floriferous habit with peak bloom in Southern California the last week of April and first weeks of May. Recurring flowering appears in the fall in Southern California producing smaller blooms.

*Size.*—2 cm to 2.5 cm (⅞-1 inch) in diameter.

*Texture.*—Firm medium texture.

*Corolla tube.*—1 cm (⅜") in length.

*Corolla lobes.*—Generally 4, occasionally vary 3 to 5 lobes.

*Corolla lobe color.*—At anthesis — above Hyacinth Blue 40/2,—below Orchid Purple 31/2.

*Corolla lobe margins.*—Entire, slightly undulate.

*Corolla lobe size.*—1.3 cm (½") long and 0.6 to 0.9 cm (2/8-⅜") wide.

*Calyx.*—0.3 cm (⅛") in length.

*Stamens.*—2 in number included within corolla tube.

Bud: Unexpanded.

*Size.*—1.2 cm (½") in length.

*Color.*—Pansy Violet 033/1 with darker shades of Pansy Violet 033.

Inflorescence:

*Size.*—12.7 cm (5") in length with 8.8 cm (3½") in width.

Foliage:

*Size.*—11.5 cm-7.6 cm (4½"-3") in length 8.2 cm-6.3 cm (3¼"-2½") in width.

*Shape.*—Ovate, base slightly cordate, tip wide acuminate.

*Color.*—Upper: 0960/2 Spinach Green maturing to Ivy Green 0001060/3. Lower: 0960/3 Spinach Green.

*Margins.*—Entire.

*Texture.*—Medium.

*Arrangement.*—Opposite.

*Pubescence.*—Both sides glabrous.

*Petiole.*—Varying from 3 cm-2 cm (1¼"-¾") in length.

I claim:

1. A new and distinct selection of *Syringa vulgaris* as substantially shown and described herein, that is characterized particularly as a novelty by the unique combination of profuse blooming at an early age, flowering well in hot areas with little winter chilling required, or flowering well in the colder typical lilac growing areas and the two toned coloring of the purple buds that open to deep purple blue flowers.

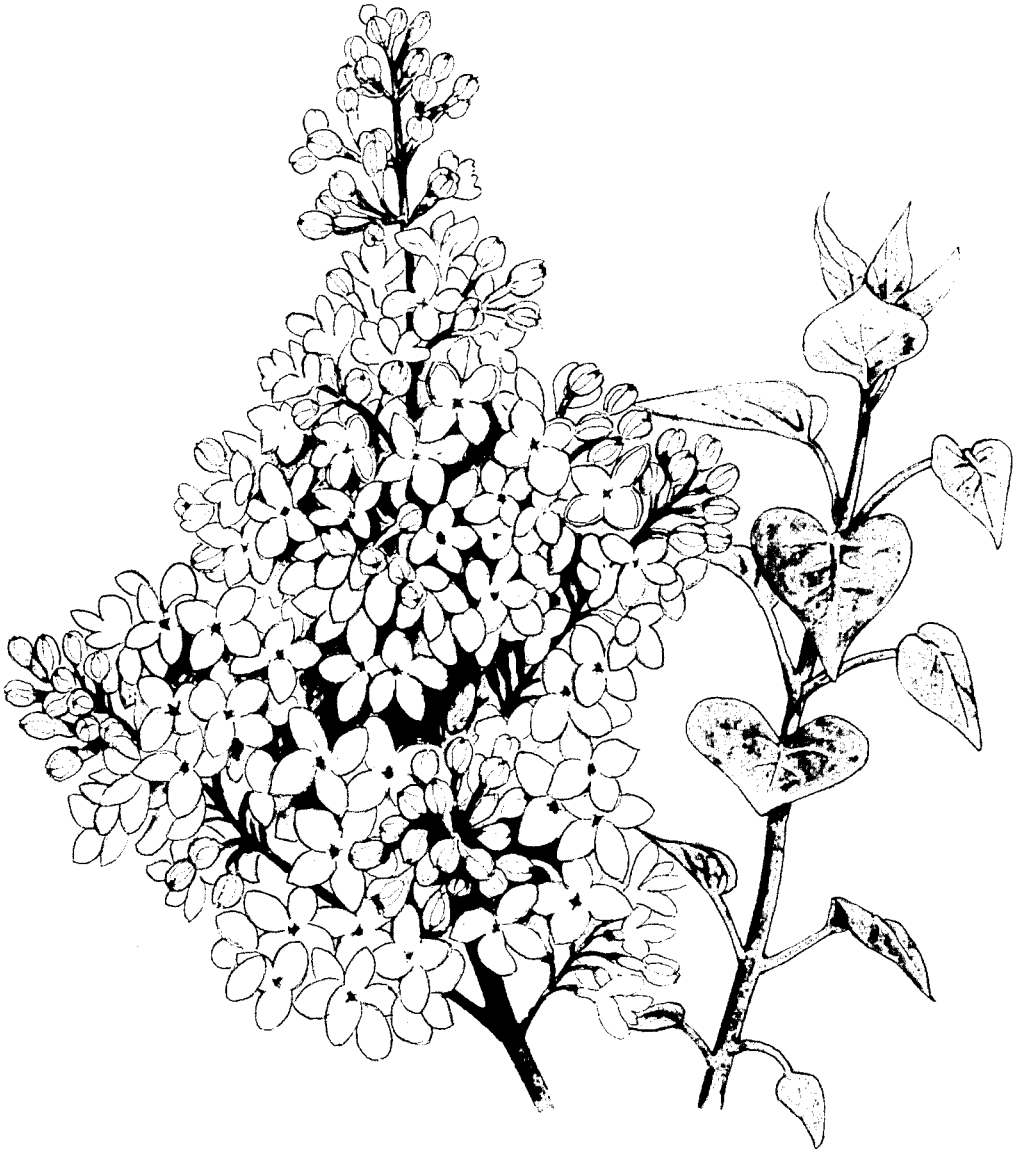

* * * * *